United States Patent [19]

Knudsen

[11] Patent Number: 4,775,411
[45] Date of Patent: Oct. 4, 1988

[54] CERTAIN SUBSTITUTED 3-AMINO-2-BENZOYLCYCLOHEX-2-ENONES

[75] Inventor: Christopher G. Knudsen, Berkeley, Calif.

[73] Assignee: Stauffer Chemica Company, Westport, Conn.

[21] Appl. No.: 872,079

[22] Filed: Jun. 9, 1986

[51] Int. Cl.$^4$ ............................................. A01N 33/02
[52] U.S. Cl. ........................................ 71/121; 71/88; 71/98; 71/103; 71/105; 71/123; 564/181; 564/221; 564/305; 564/306; 564/322; 564/440; 564/441; 564/442; 560/57; 568/305
[58] Field of Search ................. 71/123, 121; 568/329; 564/322, 305

[56] References Cited

FOREIGN PATENT DOCUMENTS 0186118  7/1985  European Pat. Off. ............. 71/123

OTHER PUBLICATIONS

Tamura, Y. et al, "Photochemical Dealkylation, etc" *Chem. Pharm. Bull.* pp. 1692–1696 (1982).

*Primary Examiner*—Glennon H. Hollrah
*Assistant Examiner*—Amelia Owens
*Attorney, Agent, or Firm*—Edwin H. Basker

[57] ABSTRACT

A compound of the formula

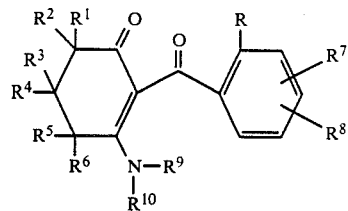

wherein R is halogen, $C_1$–$C_2$ alkyl, $C_1$–$C_2$ alkoxy, nitro; cyano; $C_1$–$C_2$ haloalkyl, or $R^aSO_n$- wherein n is 0 or 2 and $R^a$ is $C_1$–$C_2$ alkyl; $R^1$ is hydrogen or $C_1$–$C_4$ alkyl; $R^2$ is hydrogen or $C_1$–$C_4$ alkyl; or $R^1$ and $R^2$ together are alkylene having 2 to 5 carbon atoms; $R^3$ is hydrogen or $C_1$–$C_4$ alkyl; $R^4$ is hydrogen or $C_1$–$C_4$ alkyl; or $C^3$ and $R^4$ are oxo; $R^5$ is hydrogen or $C_1$–$C_4$ alkyl; $R^6$ is hydrogen or $C_1$–$C_4$ alkyl; and $R^7$ and $R^8$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^bSO_n$- wherein n is the integer 0, 1 or 2; and $R^b$ is (a) $C_1$–$C_4$ alkyl; (b) $C_1$–$C_4$ alkyl substituted with halogen or cyano; (c) phenyl; or (d) benzyl; (10) —$NR^cR^d$ wherein $R^c$ and $R^d$ independently are hydrogen or $C_1$–$C_4$ alkyl; (11) $R^eC(O)$— wherein $R^e$ is $C_1$–$C_4$ alkyl or $C_1$–$C_4$ alkogxy; (12) $SO_2NR^cR^d$ wherein $R^c$ and $R^d$ are as defined; or (13) —$N(R^c)C(O)R^d$ wherein $R^c$ and $R^d$ are as defined; $R^9$ is hydrogen or $C_1$–$C_4$ alkyl, $R^{10}$ is (a) hydrogen; (b) $C_1$–$C_6$ alkyl, (c) $C_4$–$C_6$ cycloalkyl, (d) substituted $C_1$–$C_6$ alkyl, (e) phenyl; (f) substituted phenyl; (g) $C_1$–$C_6$ alkoxy; (h) benzyl; (i) phenethyl; (j) $C_1$–$C_4$ alkyl-C(O)-; (k) $C_1$–$C_4$ alkyoxy-C(O)-; (1) $C_2$–$C_6$ alkenyl; or (m) $C_2$–$C_6$ alkynyl; and $R^9$ and $R^{10}$ together form a heterocyclic ring with the nitrogen to which they are attached containing 0, 1 or 2 additional hetero atoms (nitrogen, sulfur or oxygen).

24 Claims, No Drawings

CERTAIN SUBSTITUTED 3-AMINO-2-BENZOYLCYCLOHEX-2-ENONES

BACKGROUND OF THE INVENTION

Compounds having the structural formula

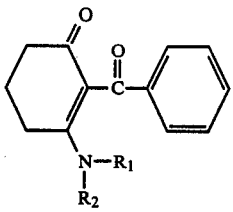

wherein $R_1$ and $R_2$ are hydrogen or alkyl are described in *Chem. Pharm. Bull.*, 30(5), 1692–1696 (1982). No utility is taught for the compounds.

DESCRIPTION OF THE INVENTION

This invention relates to 3-amino-2-benzoylcyclohex-2-enones and their use as herbicides.

One embodiment of this invention is an herbicidal composition comprising an herbicidally active substituted 3-amino-2-benzoylcyclohex-2-enones and an inert carrier therefor wherein the 2-position of the benzoyl moiety is substituted as herein recited and the 4-position preferably is substituted with an electron withdrawing group, such as halogen, cyano, trifluoromethyl or nitro. The 4-, 5- and 6-positions of the cyclohex-2-enone moiety can be substituted, preferably with the groups hereinafter recited. More preferably, the cyclohex-2-enone moiety has no substitution or the 4- or 6-positions are substituted with one or two methyl groups. The 3-, 4- and 5-positions of the benzoyl moiety can be substituted, preferably with the groups hereinafter recited.

Also embodied within the scope of this invention are novel compounds having the following structural formula

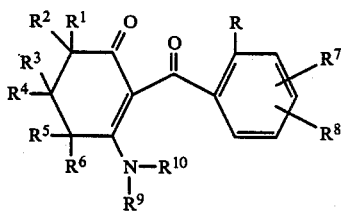

wherein

R is halogen; $C_1$-$C_2$ alkyl, preferably methyl; $C_1$-$C_2$ alkoxy, preferably methoxy; nitro; cyano; $C_1$-$C_2$ haloalkyl, preferably trifluoromethyl; or $R^aSO_n$— wherein n is 0 or 2, preferably 2 and $R^a$ is $C_1$-$C_2$ alkyl, preferably methyl. Preferably, R is chlorine, bromine, $C_1$-$C_2$ alkyl, $C_1$-$C_2$ alkoxy, cyano, nitro, $C_1$-$C_2$ alkylthio or $C_1$-$C_2$ alkylsulfonyl; more preferably chlorine, nitro, methyl, trifluoromethyl or methylsulfonyl;

$R^1$ is hydrogen or $C_1$-$C_4$ alkyl, preferably $C_1$-$C_2$ alkyl, more preferably methyl, most preferably $R^1$ is hydrogen or methyl;

$R^2$ is hydrogen; $C_1$-$C_4$ alkyl, preferably $C_1$-$C_2$ alkyl, more preferably methyl, most preferably $R^2$ is hydrogen or methyl; or $R^1$ and $R^2$ together are alkylene having 2 to 5 carbon atoms;

$R^3$ is hydrogen or $C_1$-$C_4$ alkyl, preferably $C_1$-$C_2$ alkyl, more preferably methyl; most preferably $R^3$ is hydrogen or methyl;

$R^4$ is hydrogen or $C_1$-$C_4$ alkyl, preferably $C_1$-$C_2$ alkyl, more preferably methyl; most preferably $R^4$ is hydrogen or methyl; or $R^3$ and $R^4$ together are oxo;

$R^5$ is hydrogen or $C_1$-$C_4$ alkyl, preferably $C_1$-$C_2$ alkyl, more preferably methyl; most preferably $R^5$ is hydrogen or methyl;

$R^6$ is hydrogen or $C_1$-$C_4$ alkyl, preferably $C_1$-$C_2$ alkyl, more preferably methyl, most preferably $R^6$ is hydrogen; or $R^5$ and $R^6$ together are alkylene having 2 to 5 carbon atoms;

$R^7$ and $R^8$ independently are (1) hydrogen; (2) halogen, preferably chlorine, fluorine or bromine; (3) $C_1$-$C_4$ alkyl, preferably methyl; (4) $C_1$-$C_4$ alkoxy, preferably methoxy; (5) trifluoromethoxy; (6) cyano; (7) nitro; (8) $C_1$-$C_4$ haloalkyl, more preferably trifluoromethyl; (9) $R^bSO_n$— wherein n is the integer 0, 1 or 2, preferably 2; and $R^b$ is (a) $C_1$-$C_4$ alkyl, preferably methyl;

(b) $C_1$-$C_4$ alkyl substituted with halogen or cyano, preferably chloromethyl, trifluoromethyl or cyanomethyl;

(c) phenyl; or (d) benzyl;

(10) —$NR^cR^d$ wherein $R^c$ and $R^d$ independently are hydrogen or $C_1$-$C_4$ alkyl;

(11) $R^eC(O)$— wherein $R^e$ is $C_1$-$C_4$ alkyl or $C_1$-$C_4$ alkoxy;

(12) —$SO_2NR^cR^d$ wherein $R^c$ and $R^d$ are as defined;

(13) —$N(R^c)C(O)R^d$ wherein $R^c$ and $R^d$ are as defined; and $R^9$ is hydrogen or $C_1$-$C_4$ alkyl, preferably methyl or ethyl;

$R^{10}$ is (a) hydrogen;

(b) $C_1$-$C_6$ alkyl, preferably $C_1$-$C_2$ alkyl;

(c) $C_4$-$C_6$ cycloalkyl;

(d) substituted $C_1$-$C_6$ alkyl, preferably $C_1$-$C_4$ alkyl wherein the substitutions are halogen, hydrogen, cyano, or carboxy;

(e) phenyl;

(f) substituted phenyl;

(g) $C_1$-$C_6$ alkoxy, preferably $C_1$-$C_4$ alkoxy;

(h) benzyl;

(i) phenethyl;

(j) $C_1$-$C_4$ alkyl-C(O)-;

(k) $C_1$-$C_4$ alkoxy-C(O)-;

(l) $C_2$-$C_6$ alkenyl, preferably $C_3$-$C_4$ alkenyl; or more preferably allyl and methallyl; or (m) $C_2$-$C_6$ alkynyl; or $R^9$ and $R^{10}$ together form a heterocyclic ring with the nitrogen to which they are attached containing 0, 1 or 2 additional hetero atoms (nitrogen, sulfur or oxygen).

The term "$C_1$-$C_4$ alkyl" includes methyl, ethyl, n-propyl, isopropyl, n-butyl, sec-butyl, isobutyl and t-butyl. The term "halogen" includes chlorine, bromine, iodine and fluorine. The term "$C_1$-$C_4$ alkoxy" includes methoxy, ethoxy, n-propoxy, isopropoxy, n-butoxy, sec-butoxy, isobutoxy and t-butoxy. The term "$C_1$-$C_4$ haloalkyl" includes the alkyl groups defined above under $C_1$–$C_4$ alkyl in which one or more hydrogen is replaced by chloro, bromo, iodo or fluoro.

Preferably $R^7$ is in the 3-position. More preferably $R^7$ is hydrogen, chorine, fluorine, trifluoromethyl, cyano, $C_1$–$C_4$ alkoxy, or $C_1$–$C_4$ thioalkyl. More preferably, $R^7$ is hydrogen. Preferably $R^8$ is in the 4-position. Most preferably $R^8$ is halogen, cyano, trifluoromethyl, or $R^bSO_2$ wherein $R^b$ is $C_1$–$C_4$ alkyl, preferably methyl or $C_1$–$C_4$ haloalkyl, preferably chloromethyl, difluoromethyl or trifluoromethyl.

The compounds of this invention are active herbicides of a general type. That is, they are herbicidally effective against a wide range of plant species. The method of controlling undesirable vegetation of the present invention comprises applying an herbicidally effective amount of the above-described compounds to the area where control is desired.

The compounds of the present invention can be prepared by the following two-step general method.

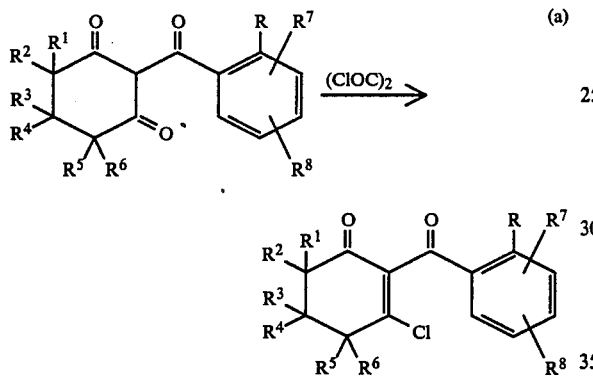

(a)

wherein R through $R^8$ are as defined.

Generally in step (a) the benzoyl dione is dissolved in an inert solvent such as methylene dichloride and an excess, usually 150 to 200 mole percent, of oxalyl chloride is added followed by a catalytic amount (0.1 equivalent) of dimethylformamide. The reaction mixture is stirred from one hour to one day at room temperature. The reaction product is isolated using conventional techniques.

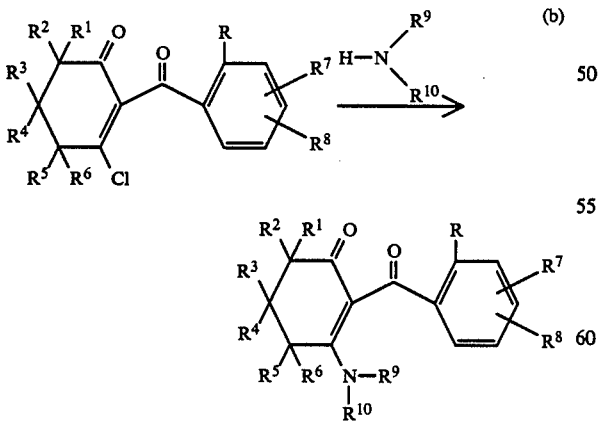

(b)

wherein R through $R^{10}$ are as defined.

Generally, in step (b) the 3-chloro-2-benzoylcycloalk-2-enone is reacted with 200 to 250 mole percent of primary or secondary amine in an inert solvent. The mixture is stirred 1 to 18 hours and the product is isolated using conventional techniques.

The precursor benzoyl diones used in step (a) can be prepared by the following two-step general method.

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

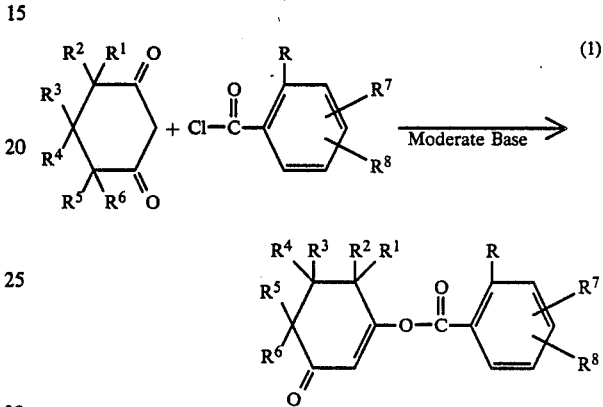

wherein R through $R^8$ are as defined and the moderate base is as defined, preferably tri-$C_1$–$C_6$ alkylamine, alkali metal carbonate or alkali metal phosphate.

Generally, in step (1) mole amounts of the dione and substituted benzoyl reactant are used, along with a mole amount or excess of the base. The two reactants are combined in an organic solvent such as methylene chloride, toluene, ethyl acetate or dimethylformamide. The base or benzoyl reactant preferably is added to the reaction mixture with cooling. The mixture is stirred at 0° C.–50° C. until the reaction is substantially complete.

The reaction product is worked up by conventional techniques.

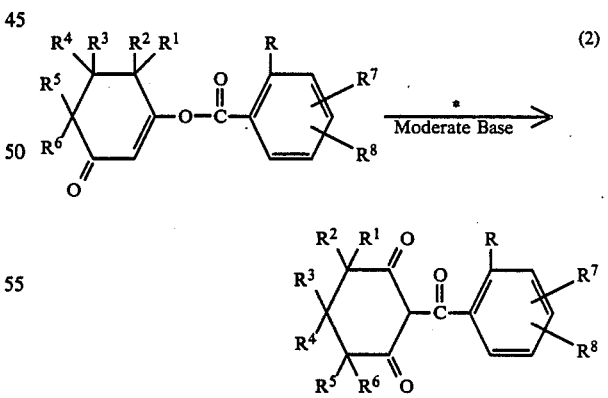

*Cyanide source.
Moderate Base = as defined herein.

wherein R through $R^8$ are as defined.

Generally, in step (2) a mole of the enol ester intermediate is reacted with 1 to 4 moles of the moderate base, preferably about 2 moles of moderate base and from 0.01 mole to about 0.5 mole or higher, preferably about 0.1 mole of the cyanide source (e.g., potassium cyanide or acetone cyanohydrin). The mixture is stirred in a reaction pot until the rearrangement is substantially complete at a temperature below 80° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; cyanohydrins of benzaldehyde or of $C_2$-$C_5$ aliphatic aldehydes such as acetaldehyde, propionaldehyde, etc., cyanohydrins; zinc cyanide; tri(-lower alkyl) silyl cyanides, notably trimethyl silyl cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1-10 mole % of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic bases such as tertiary amines and inorganic bases such as alkali metal carbonates and phosphates. Suitable tertiary amines include trialkylamines such as triethylamine. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the Crown ethers.

A number of different solvents are useful in this process, depending on the nature of the acid chloride or the acylated product. A preferred solvent for this reaction is 1,2-dichloroethane. Other solvents which can be employed, depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

The above described substituted benzoyl chlorides can be prepared from the corresponding substituted benzoic acids according to the teaching of *Reagents for Organic Synthesis*, Vol. I, L. F. Fieser and M. Fieser, pp. 767-769 (1967).

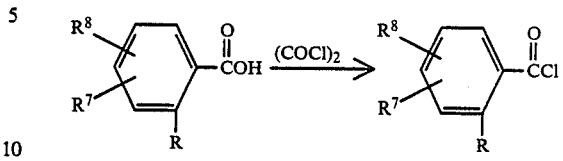

wherein R, $R^7$ and $R^8$ are as previously defined.

The substituted benzoic acids can be prepared by a wide variety of general methods according to the teaching of *The Chemistry of Carboxylic Acids and Esters*, S. Patai, editor, J. Wiley and Sons, New York, N.Y. (1969) and *Survey of Organic Synthesis*, C. A. Buehler and D. F. Pearson, J. Wiley and Sons, (1970).

The following are four representative examples of the methods described therein.

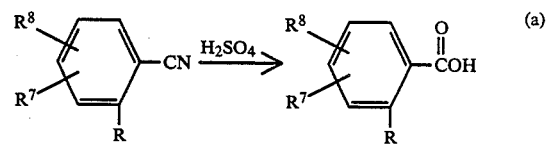

wherein R, $R^7$ and $R^8$ are as previously defined.

In reaction (a) the substituted benzonitrile is heated to reflux in aqueous sulfuric acid for several hours. The mixture is cooled and the reaction product is isolated by conventional techniques.

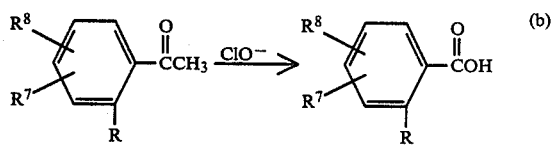

wherein R, $R^7$ and $R^8$ are as previously defined.

In reaction (b) the substituted acetophenone is heated to reflux for several hours in an aqueous hypochlorite solution. The mixture is cooled and the reaction product is isolated by conventional techniques.

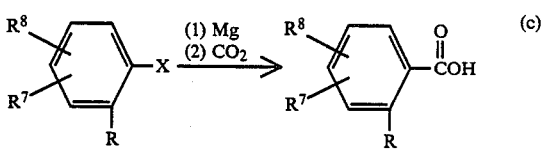

wherein R, $R^7$ and $R^8$ are as defined and X is chlorine, bromine or iodine.

The substituted aromatic halide is allowed to react with magnesium in a solvent such as ether. The solution is then poured over crushed dry ice and the benzoic acid is isolated by conventional techniques.

The following examples teach the synthesis of a representative compound of this invention.

EXAMPLE I 2-(2-Chloro-4-methanesulfonylbenzoyl)-cyclohexane-1,3-dione

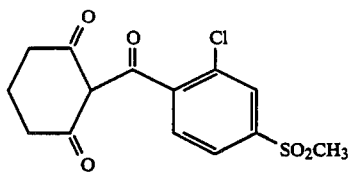

1,3-Cyclohexanedione [11.2 grams (g), 0.1 mole] and 23.3 g (0.1 mole) 2-chloro-4-methanesulfonylbenzoyl chloride were dissolved in 200 ml methylene chloride at room temperature. Triethylamine (11 g, 0.11 mole) was slowly added with cooling. The reaction mixture was stirred at room temperature for 5 hours and then poured into 2N hydrochloric acid. The aqueous phase was discarded and the organic phase dried with MgSO4 and then evaporated to yield the intermediate enol ester 3-(2-chloro-4-methanesulfonylbenzoyloxy)cyclohex-2-enone. The 3-(2-chloro-4-methanesulfonylbenzoyloxy)-cyclohex-2-enone was dissolved in 200 ml acetonitrile and triethylamine (22 g, 0.22 mole) was added all at once, followed by acetonecyanohydrin (0.8 g, 0.01 mole). The solution was stirred for 5 hours and then poured into 2N HCl and extracted twice with ethyl acetate. The organic layer was dried with MgSO4 and the solvent evaporated to yield the product.

EXAMPLE II

3-Chloro-2-(2-chloro-4-methanesulfonylbenzoyl)cyclohex-2-enone

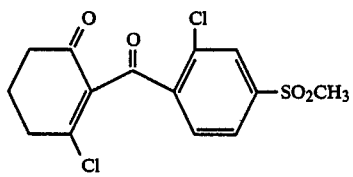

2-(2-Chloro-4-methanesulfonylbenzoyl)-cyclohexane-1,3-dione [9.8 g, 30 millimole (mmol)] was dissolved in 100 ml methylene chloride and stirred at room temperature. To this solution was added oxalyl chloride (5.7 g, 45 mmol) followed by dimethylformamide (0.5 ml) in portions small enough to control effervescence. The resulting solution was stirred for 4 hours and then poured into water and extracted with methylene chloride. The organic layer was washed again with water, saturated K2CO3 solution and then dried with MgSO4 and the solvent evaporated to yield 3-chloro-2(2-chloro-4-methanesulfonylbenzoyl)cyclohex-2-enone (7.3 g, 70%) as an oil which was used without further purification.

EXAMPLE III 2-(2-Chloro-4-methanesulfonylbenzoyl)-3-N-methyl, N-methoxyamino-cyclohex-2-enone

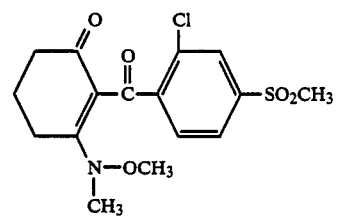

3-Chloro-2-(2-chloro-4-methanesulfonylbenzoyl)-cyclohex-2-enone (8.0 g, 23 millimole) was dissolved in 80 ml THF and stirred at room temperature. N,O-Dimethylhydroxylamine hydrochloride (2.5 g, 27 millimole) and triethylamine (4.6 g, 46 millimole) were added all at once, and the reaction mixture stirred for 4 hours. The reaction mixture was then poured into 1N HCl solution and extracted with ethyl acetate. The organic layer was washed with 5% K2CO3, dried with MgSO4 and the solvent evaporated to yield a solid: 2.2 g, 27%, m.p. 109°–112° C. The structure is consistent with nuclear magnetic resonance, infrared and mass spectral data.

The following is a table of certain selected compounds that are preparable according to the procedure described herein. Compound numbers are assigned to each compound and are used throughout the remainder of the application.

TABLE I

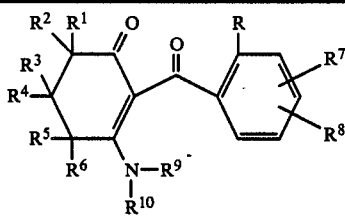

| Comp. No. | R | $R^1$ | $R^2$ | $R^3$ | $R^4$ | $R^5$ | $R^6$ | $R^7$ | $R^8$ | $R^9$ | $R^{10}$ |
|---|---|---|---|---|---|---|---|---|---|---|---|
| 1 | Cl | H | H | H | H | H | H | H | 4-Cl | $CH_3$ | $OCH_3$ |
| 2 | Cl | H | H | H | H | H | H | H | 4-Cl | H | $OC_2H_5$ |
| 3 | Cl | H | H | H | H | H | H | H | 4-$NO_2$ | $CH_3$ | $OCH_3$ |
| 4 | Cl | H | H | H | H | H | H | H | 4-Cl | H | $OCH_3$ |
| 5 | Cl | H | H | $CH_3$ | $CH_3$ | H | H | H | 4-$NO_2$ | $CH_3$ | $OCH_3$ |
| 6 | Cl | H | H | H | H | H | H | H | 4-$NO_2$ | $CH_3$ | $OCH_3$ |
| 7 | Cl | H | H | $CH_3$ | $CH_3$ | H | H | H | 4-$SO_2$—i-$C_3H_7$ | $CH_3$ | $OCH_3$ |
| 8 | Cl | H | H | H | H | H | H | H | 4-$SO_2$—i-$C_3H_7$ | $CH_3$ | $OCH_3$ |
| 9 | Cl | H | H | H | H | H | H | H | 4-$SO_2$—n-$C_4H_9$ | $CH_3$ | $OCH_3$ |
| 10 | $NO_2$ | H | H | $CH_3$ | $CH_3$ | H | H | H | 4-Cl | $CH_3$ | $OCH_3$ |
| 11 | $NO_2$ | $CH_3$ | $CH_3$ | H | H | H | H | H | 4-Cl | $CH_3$ | $OCH_3$ |
| 12 | $CH_3$ | H | H | H | H | H | H | H | H | $CH_3$ | $OCH_3$ |
| 13 | Cl | H | H | H | H | H | H | H | 4-Cl | $CH_3$ | $CH_3$ |
| 14 | Cl | H | H | H | H | H | H | H | 4-Cl | $CH_3$ | H |

TABLE I-continued

| Comp. No. | R | $R^1$ | $R^2$ | $R^3$ | $R^4$ | $R^5$ | $R^6$ | $R^7$ | $R^8$ | $R^9$ | $R^{10}$ |
|---|---|---|---|---|---|---|---|---|---|---|---|
| 15 | Cl | H | H | H | H | H | H | H | 4-Cl | $C_2H_5$— | H |
| 16[a] | Cl | H | H | H | H | H | H | H | 4-$SO_2CH_3$ | $CH_3$ | $OCH_3$ |
| 17 | Cl | H | H | H | H | H | H | H | 4-$SO_2$—$C_2H_5$ | $CH_3$ | $OCH_3$ |
| 18 | $NO_2$ | $CH_3$ | $CH_3$ | H | H | H | H | H | H | $CH_3$ | $OCH_3$ |
| 19 | Cl | H | H | H | H | H | H | Cl | 4-$SO_2$—$C_2H_5$ | $CH_3$ | $OCH_3$ |
| 20 | Cl | H | H | H | H | H | H | H | 4-$SO_2CH_3$ | —$CH_2CH_2OCH_2CH_2$— | |
| 21 | Cl | H | H | H | H | H | H | H | 4-$SO_2CH_3$ | —$CH_2CH_2CH_2CH_2$— | |
| 22 | Cl | H | H | H | H | H | H | H | 4-$SO_2CH_3$ | —$CH_2SCH_2CH_2$— | |
| 23 | Cl | H | H | H | H | H | H | H | 4-$SO_2CH_3$ | $CH_3$ | $C_2H_5OC(O)CH_2$— |
| 24 | Cl | H | H | H | H | H | H | H | 4-$SO_2CH_3$ | $CH_3$ | $(CH_3O)_2CHCH_2$— |
| 25 | Cl | H | H | H | H | H | H | H | 4-$SO_2CH_3$ | H | $CH_2=C(CH_3)$—$CH_2$— |
| 26 | Cl | H | H | H | H | H | H | H | 4-Cl | H | $CH_2=C(CH_3)$—$CH_2$— |
| 27 | Cl | H | H | H | H | H | H | H | 4-Cl | —$CH_2SCH_2CH_2$— | |
| 28 | Cl | H | H | H | H | H | H | H | 4-Cl | $CH_3$ | $C_2H_5OC(O)CH_2$— |
| 29 | Cl | H | H | H | H | H | H | H | 4-Cl | $CH_3$ | $(CH_3O)_2CHCH_2$— |
| 30 | Cl | H | H | H | H | H | H | H | 4-Cl | $CH_3$ | $HOCH_2CH_2$— |
| 31 | $CH_3$ | H | H | H | H | H | H | H | 4-Br | $CH_3$ | $OCH_3$ |
| 32 | Cl | H | H | H | H | H | H | Cl | 4-Cl | —$CH_2CH_2CH_2CH_2$— | |
| 33 | $NO_2$ | $CH_3$ | $CH_3$ | H | H | H | H | H | H | —$CH_2CH_2CH_2CH_2$— | |
| 34 | $NO_2$ | $CH_3$ | $CH_3$ | H | H | H | H | H | H | —$CH_2CH_2OCH_2CH_2$— | |
| 35 | Cl | H | H | H | H | H | H | Cl | 4-Cl | —$CH_2CH_2OCH_2CH_2$— | |
| 36 | Cl | H | H | H | H | H | H | H | 4-$SO_2CH_3$ | $CH_3$ | $HOCH_2CH_2$— |
| 37 | Cl | H | H | H | H | H | H | H | 4-Cl | H | H |
| 38 | $NO_2$ | $CH_3$ | $CH_3$ | H | H | H | H | H | 4-$CF_3$ | $C_2H_5$ | $C_2H_5$ |
| 39 | $CH_3$ | $CH_3$ | $CH_3$ | H | H | H | H | H | 4-$SO_2C_2H_5$ | $C_2H_5$ | $C_2H_5$ |
| 40 | Cl | H | H | H | H | H | H | H | 4-Cl | $CH_3$ | phenyl |
| 41 | Cl | H | H | H | H | H | H | H | 4-$SO_2CH_3$ | $CH_3$ | phenyl |
| 42 | Cl | H | H | H | H | H | H | H | 4-Cl | $CH_3$ | benzyl |
| 43 | Cl | H | H | H | H | H | H | H | 4-Cl | H | phenyl |
| 44 | Cl | H | H | H | H | H | H | H | 4-Cl | Et | $(CH_3)_2CHCH(CH_3)$— |
| 45 | Cl | H | H | H | H | H | H | H | 4-Cl | $CH_3$ | cyclopentyl |
| 46 | Cl | H | H | H | H | H | H | H | 4-Cl | H | —$CH_2CN$ |
| 47 | $NO_2$ | H | H | H | H | H | H | H | 4-$CF_3$ | $C_2H_5$ | $C_2H_5$ |
| 48 | Cl | H | H | H | H | H | H | H | 4-$SO_2CH_3$ | $CH_3$ | benzyl |
| 49 | Cl | H | H | H | H | H | H | H | 4-$SO_2CH_3$ | $C_2H_5$ | $(CH_3)_2CHCH(CH_3)$— |
| 50 | Cl | H | H | H | H | H | H | H | 4-$SO_2CH_3$ | $CH_3$ | cyclopentyl |
| 51 | Cl | H | H | H | H | H | H | H | 4-$SO_2CH_3$ | $CH_3$ | $HCC$—$CH_2$— |
| 52 | Cl | H | H | H | H | H | H | H | 4-Cl | $CH_3$ | $NC$—$CH_2CH_2$— |
| 53 | Cl | H | H | H | H | H | H | H | 4-$SO_2CH_3$ | $CH_3$ | $NC$—$CH_2CH_2$— |
| 54 | Cl | H | H | H | H | H | H | H | 4-Cl | —$CH_2CH_2N(CH_3)$—$CH_2CH_2$— | |
| 55 | Cl | H | H | H | H | H | H | H | 4-Cl | $CH_3$ | $PhCH_2CH_2$— |
| 56 | Cl | H | H | H | H | H | H | H | 4-$SO_2CH_3$ | $CH_3$ | $PhCH_2CH_2$— |
| 57 | $NO_2$ | $CH_3$ | $CH_3$ | H | H | H | H | H | 4-Cl | $C_2H_5$ | $C_2H_5$ |
| 58 | Cl | H | H | H | H | H | H | H | 4-Cl | H | $HOCH_2CH_2$— |

TABLE I-continued

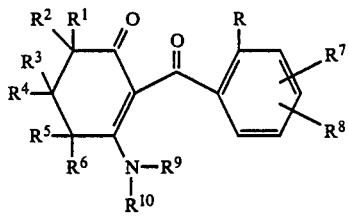

| Comp. No. | R | R¹ | R² | R³ | R⁴ | R⁵ | R⁶ | R⁷ | R⁸ | R⁹ | R¹⁰ |
|---|---|---|---|---|---|---|---|---|---|---|---|
| 59 | ·NO₂ | H | H | H | H | H | H | H | 4-Cl | C₂H₅ | C₂H₅ |
| 60 | CH₃ | CH₃ | CH₃ | H | H | H | H | H | 4-Br | C₂H₅ | C₂H₅ |
| 61 | NO₂ | H | H | H | H | H | H | H | 4-Cl | CH₃ | OCH₃ |
| 62 | NO₂ | H | H | H | H | H | H | H | H | CH₃ | OCH₃ |
| 63 | Cl | H | H | H | H | H | H | H | 4-Cl | C₂H₅ | C₂H₅ |
| 64 | NO₂ | CH₃ | CH₃ | H | H | H | H | H | H | CH₃ | CH₃ |
| 65 | NO₂ | CH₃ | CH₃ | H | H | H | H | H | H | CH₃ | H |
| 66 | NO₂ | CH₃ | CH₃ | H | H | H | H | H | H | C₂H₅ | C₂H₅ |
| 67 | Cl | H | H | H | H | H | H | H | 4-SO₂CH₃ | C₂H₅ | C₂H₅ |
| 68 | Cl | CH₃ | CH₃ | oxo | CH₃ | CH₃ | H | 4-CH₃SO₂ | —CH₂CH₂O—CH₂CH₂— | |
| 69 | NO₂ | CH₃ | CH₃ | oxo | CH₃ | CH₃ | H | H | C₂H₅ | C₂H₅ |
| 70 | H | CH₃ | CH₃ | oxo | CH₃ | CH₃ | H | H | CH₃ | CH₂CH(OCH₃)₂ |
| 71 | H | CH₃ | CH₃ | oxo | CH₃ | CH₃ | H | 4-Cl | C₂H₅ | C₂H₅ |

(a)Prepared in Example III.

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence herbicide test. On the day preceding treatment, seeds of seven different weed species are planted in loamy sand soil in individual rows using one species per row across the width of a flat. The weeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*) and yellow nutsedge (YNS) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests are shown in the following Table II.

TABLE II

Pre-Emergence Herbicidal Activity
Application Rate - 4.48 kg/ha

| Cmpd. No. | FT | WG | WO | AMG | VL | MD | YNS |
|---|---|---|---|---|---|---|---|
| 1 | 80 | 90 | 0 | 30 | 100 | 85 | 80 |
| 2 | 25 | 35 | 0 | 0 | 50 | 0 | 20 |
| 3 | 100 | 75 | 20 | 20 | 100 | 95 | 75 |
| 4 | 20 | 20 | 0 | 0 | 25 | 20 | 0 |
| 5 | 100 | 100 | 30 | 40 | 100 | 100 | 90 |
| 6 | 40 | 100 | 0 | 0 | 100 | 100 | 0 |
| 7 | 0 | 25 | 0 | 0 | 50 | 100 | 0 |
| 8 | 0 | 30 | 0 | 40 | 90 | 100 | 90 |
| 9 | 20 | 90 | 0 | 100 | 100 | 100 | 80 |
| 10 | 100 | 90 | 40 | 100 | 100 | 100 | 90 |
| 11 | 100 | 100 | 70 | 100 | 100 | 100 | 90 |
| 12 | 50 | 0 | 0 | 0 | 0 | 0 | 0 |
| 13 | 0 | 100 | 0 | 5 | 100 | 95 | 70 |
| 14 | 0 | 90 | 0 | 0 | 100 | 100 | 50 |
| 15 | 0 | 40 | 0 | 0 | 0 | 0 | 40 |
| 16 | 100 | 100 | 100 | 100 | 100 | 100 | 80 |
| 17 | 95 | 100 | 80 | 100 | 100 | 100 | 80 |
| 18 | 100 | 100 | 90 | 50 | 100 | 100 | 80 |
| 19 | 100 | 100 | 30 | 100 | 100 | 100 | 80 |
| 20 | 100 | 100 | 80 | 100 | 100 | 100 | 80 |
| 21 | 0 | 65 | 0 | 25 | 100 | 90 | 80 |
| 22 | 100 | 100 | 50 | 100 | 100 | 100 | 80 |
| 23 | 100 | 100 | 80 | 100 | 100 | 100 | 80 |
| 24 | 100 | 100 | 80 | 100 | 100 | 100 | 80 |
| 25 | 0 | 0 | 0 | 0 | 100 | 50 | 80 |
| 26 | 10 | 40 | 0 | 0 | 100 | 95 | 80 |
| 27 | 100 | 100 | 40 | 100 | 100 | 100 | 80 |
| 28 | 100 | 100 | 20 | 50 | 100 | 100 | 80 |
| 29 | 100 | 100 | 50 | 100 | 100 | 100 | 80 |
| 30 | 100 | 100 | 50 | 90 | 100 | 100 | 80 |
| 31 | 5 | 70 | 0 | 20 | 100 | 100 | 80 |
| 32 | 5 | 40 | 10 | 0 | 100 | 85 | 60 |
| 33 | 5 | 50 | 10 | 0 | 0 | 0 | 20 |
| 34 | 100 | 100 | 95 | 75 | 100 | 100 | 80 |
| 35 | 100 | 100 | 10 | 75 | 100 | 100 | 80 |
| 36 | 100 | 100 | 90 | 100 | 100 | 100 | 80 |

TABLE II-continued

Pre-Emergence Herbicidal Activity
Application Rate - 4.48 kg/ha

| Cmpd. No. | FT | WG | WO | AMG | VL | MD | YNS |
|---|---|---|---|---|---|---|---|
| 37 | 0 | 100 | 0 | 10 | 100 | 100 | 80 |
| 38 | 100 | 100 | 85 | 100 | 100 | 100 | 80 |
| 39 | 100 | 100 | 80 | 100 | 100 | 100 | 80 |
| 40 | 0 | 80 | 0 | 5 | 90 | 90 | 70 |
| 41 | 100 | 100 | 80 | 100 | 100 | 100 | 80 |
| 42 | 95 | 98 | 10 | 100 | 100 | 100 | 80 |
| 43 | 0 | 0 | 0 | 5 | 10 | 20 | 0 |
| 44 | 5 | 85 | 0 | 0 | 100 | 100 | 80 |
| 45 | 30 | 85 | 0 | 10 | 100 | 100 | 80 |
| 46 | 100 | 100 | 10 | 100 | 100 | 100 | 80 |
| 47 | 100 | 100 | 80 | 100 | 100 | 100 | 80 |
| 48 | 100 | 100 | 30 | 100 | 100 | 100 | 80 |
| 49 | 10 | 100 | 0 | 100 | 100 | 100 | 80 |
| 50 | 100 | 100 | 10 | 100 | 100 | 100 | 80 |
| 51 | 100 | 100 | 80 | 80 | 100 | 100 | 80 |
| 52 | 100 | 100 | 10 | 100 | 100 | 100 | 80 |
| 53 | 100 | 100 | 80 | 100 | 100 | 100 | — |
| 54 | 100 | 100 | 30 | 100 | 100 | 100 | 80 |
| 55 | 100 | 100 | 5 | 80 | 100 | 100 | 80 |
| 56 | 100 | 100 | 30 | 100 | 100 | 100 | 80 |
| 57 | 100 | 100 | 80 | 100 | 100 | 100 | 80 |
| 58 | 0 | 20 | 0 | 0 | 100 | 90 | 80 |
| 59 | 100 | 100 | 70 | 70 | 100 | 100 | 80 |
| 60 | 100 | 100 | 0 | 5 | 100 | 100 | 80 |
| 68 | 100 | 100 | 100 | 100 | 100 | 100 | 80 |
| 69 | 100 | 100 | 100 | 100 | 100 | 100 | 80 |
| 70 | 100 | 100 | 95 | 100 | 100 | 100 | 80 |
| 71 | 100 | 100 | 100 | 100 | 100 | 100 | 80 |

(—) = Not tested.

Post-emergence Herbicide Test: This test is conducted in an identical manner to the testing procedure for the pre-emergence herbicide test, except the seeds of the seven different weed species are planted 10–12 days before treatment. Also, watering of the treated flats is confined to the soil surface and not to the foilage of the sprouted plants.

The results of the post-emergence herbicide test are reported in Table III.

TABLE III

Post-Emergence Herbicidal Activity
Application Rate - 4.48 kg/ha

| Cmpd. No. | FT | WG | WO | AMG | VL | MD | YNS |
|---|---|---|---|---|---|---|---|
| 1 | 80 | 100 | 20 | 100 | 100 | 100 | 50 |
| 2 | 65 | 50 | 0 | 40 | 75 | 75 | 15 |
| 3 | 50 | 60 | 10 | 50 | 100 | 100 | 60 |
| 4 | 0 | 20 | 10 | 25 | 50 | 40 | 0 |
| 5 | 90 | 70 | 50 | 40 | 80 | 80 | 60 |
| 6 | 20 | 60 | 0 | 35 | 100 | 100 | 30 |
| 7 | 10 | 60 | 0 | 50 | 50 | 90 | 0 |
| 8 | 50 | 40 | 20 | 50 | 100 | 100 | 80 |
| 9 | 0 | 100 | 0 | 100 | 100 | 100 | 80 |
| 10 | 90 | 100 | 30 | 50 | 65 | 70 | 65 |
| 11 | 100 | 100 | 70 | 100 | 100 | 100 | 80 |
| 12 | 10 | 0 | 0 | 10 | 40 | 10 | 0 |
| 13 | 0 | 10 | 65 | 95 | 100 | 95 | 30 |
| 14 | 0 | 20 | 0 | 90 | 95 | 80 | 30 |
| 15 | 0 | 20 | 0 | 90 | 95 | 80 | 10 |
| 16 | 100 | 95 | 100 | 90 | 100 | 100 | 80 |
| 17 | 85 | 100 | 65 | 90 | 90 | 100 | 80 |
| 18 | 85 | 65 | 90 | 40 | 85 | 80 | 80 |
| 19 | 100 | 100 | 80 | 90 | 90 | 100 | 80 |
| 20 | 100 | 100 | 100 | 100 | 100 | 100 | 70 |
| 21 | 80 | 100 | 0 | 100 | 95 | 100 | — |
| 22 | 100 | 100 | 98 | 100 | 98 | 100 | 80 |
| 23 | 100 | 100 | 100 | 100 | 100 | 100 | 80 |
| 24 | 100 | 100 | 95 | 100 | 100 | 100 | 80 |
| 25 | 0 | 10 | 0 | 10 | 50 | 20 | 10 |
| 26 | 0 | 20 | 0 | 10 | 50 | 20 | 0 |
| 27 | 100 | 100 | 90 | 100 | 100 | 100 | 70 |
| 28 | 100 | 100 | 85 | 100 | 100 | 100 | 80 |
| 29 | 90 | 100 | 50 | 100 | 100 | 100 | 70 |
| 30 | 100 | 95 | 50 | 100 | 100 | 100 | 70 |
| 31 | 80 | 70 | 0 | 70 | 100 | 100 | 0 |
| 32 | 30 | 60 | 0 | 10 | 50 | 80 | 30 |
| 33 | 30 | 50 | 40 | 20 | 50 | 10 | 30 |
| 34 | 100 | 85 | 85 | 90 | 90 | 90 | 80 |
| 35 | 90 | 90 | 50 | 100 | 100 | 100 | 80 |
| 36 | 100 | 95 | 90 | 85 | 98 | 100 | 80 |
| 37 | 0 | 50 | 0 | 30 | 80 | 50 | 30 |
| 38 | 100 | 90 | 100 | 95 | 80 | 100 | 80 |
| 39 | 100 | 100 | 100 | 90 | 100 | 100 | 30 |
| 40 | 10 | 75 | 0 | 25 | 100 | 100 | 0 |
| 41 | 100 | 100 | 100 | 100 | 100 | 100 | — |
| 42 | 30 | 100 | 20 | 100 | 100 | 100 | 0 |
| 43 | 0 | 0 | 0 | 5 | 0 | 0 | 0 |
| 44 | 10 | 90 | 0 | 80 | 100 | 100 | 30 |
| 45 | 80 | 100 | 0 | 100 | 100 | 100 | 30 |
| 46 | 100 | 100 | 85 | 100 | 100 | 100 | — |
| 47 | 100 | 100 | 100 | 100 | 100 | 100 | 70 |
| 48 | 60 | 80 | 50 | 50 | 80 | 80 | 30 |
| 49 | 10 | 80 | 30 | 50 | 80 | 80 | 30 |
| 50 | 50 | 80 | 30 | 50 | 80 | 90 | 70 |
| 51 | 100 | 100 | 80 | 80 | 100 | 100 | 80 |
| 52 | 100 | 100 | 10 | 100 | 100 | 100 | 80 |
| 53 | 100 | 100 | 80 | 100 | 100 | 100 | — |
| 54 | 100 | 100 | 30 | 100 | 100 | 100 | 80 |
| 55 | 100 | 100 | 5 | 80 | 100 | 100 | 80 |
| 56 | 95 | 90 | 80 | 100 | 100 | 100 | 80 |
| 57 | 85 | 80 | 80 | 50 | 85 | 90 | 40 |
| 58 | 10 | 30 | 20 | 10 | 90 | 50 | 20 |
| 59 | 80 | 80 | 80 | 90 | 90 | 100 | 80 |
| 60 | 80 | 80 | 50 | 50 | 90 | 100 | 80 |
| 68 | 85 | 80 | 85 | 60 | 80 | 80 | 70 |
| 69 | 80 | 80 | 80 | 80 | 80 | 80 | 80 |
| 70 | 60 | 70 | 50 | 80 | 90 | 90 | 60 |
| 71 | 100 | 100 | 100 | 100 | 100 | 100 | 80 |

(—) - Not tested.

Pre-Emergence Multi-Weed Herbicide Test

Several compounds were evaluated at an application rate of ½ lb/acre (0.56 kg/ha) for pre-emergence activity against a larger number of weed species.

Pre-Emergence Multi-Weed Herbicide Test

Several compounds were evaluated at an application rate of ½ lb/acre (0.56 kg/ha) for pre-emergence activity against a larger number of weed species.

The process was generally similar to the pre-emergence herbicide test described above except that only 150 or 75 milligrams of test compound were weighed out and the application rate was 40 gallons per acre.

Redroot pigweed (PW) and curly dock (CD) were eliminated in this test and the following weed species were added:

| Grasses: | | |
|---|---|---|
| downy brome | Bromus tectorum | (DB) |
| annual ryegrass | Lolium multiflorum | (ARG) |
| shattercane | Sorghum bicolor | (SHC) |
| broadleaf signalgrass | Brachiaria platyphylla | (BSG) |
| hemp sesbania | Sesbania exaltata | (SESB) |
| sicklepod | Cassia obtusifolia | (SP) |
| cocklebur | Xanthium sp. | (CB) |

The results of the test are shown in Table IV.

TABLE IV

Pre-Emergence Multi-weed Herbicide Test
Application Rate - 0.56 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 61 | 60 | 100 | 100 | 100 | 85 | 65 | 85 | 25 | 80 | 100 | 35 | 100 | 95 | 65 |
| 62 | 60 | 100 | 75 | 80 | 75 | 20 | 70 | 25 | 90 | 100 | 0 | 100 | 50 | 50 |
| 63 | — | 25 | 25 | 100 | 30 | 0 | 50 | 25 | 50 | 100 | 25 | — | 0 | 20 |
| 64 | — | 35 | 30 | 60 | 50 | 20 | 0 | 20 | 50 | 60 | 30 | — | 35 | 100 |
| 65 | — | 100 | 60 | 80 | 60 | 20 | 0 | 25 | 35 | 50 | 0 | — | 0 | 0 |
| 66 | — | 100 | 85 | 100 | 100 | 30 | 35 | 35 | 60 | 75 | 0 | — | 50 | 100 |
| 67 | — | 80 | 80 | 100 | 85 | 20 | 80 | 95 | 100 | 100 | 45 | — | — | 100 |

(—) - Not tested.

Post-Emergence Multi-Weed Herbicide Test: This test is conducted in an identical manner to the testing procedure for the post-emergence herbicide test, except the seeds of the seven weed species used in the pre-emergence multi-weed herbicide test were used and the seeds were planted 10–12 days before treatment. Also, watering of the treated flats is confined to the soil surface and not to the foliage of the sprouted plants.

The results of the post-emergence multi-weed herbicide test are reported in Table V.

TABLE V

Post-Emergence Multi-Weed Herbicidal Activity
Application Rate - 0.56 kg/ha

| Cmpd. No. | DB | FT | ARG | WG | SHC | WO | BSG | AMG | SESB | VL | SP | MD | YNS | CB |
|---|---|---|---|---|---|---|---|---|---|---|---|---|---|---|
| 61 | 35 | 40 | 60 | 70 | 65 | 20 | 65 | 100 | 100 | 100 | 85 | 95 | 60 | 95 |
| 62 | 50 | 100 | 75 | 100 | 75 | 20 | 85 | 40 | 80 | 90 | 0 | 35 | 20 | 20 |
| 63 | — | 0 | 0 | 90 | 20 | 0 | 75 | 100 | 100 | 100 | 50 | — | 10 | 50 |
| 64 | — | 35 | 0 | 60 | 40 | 20 | 20 | 55 | 65 | 100 | 0 | — | 0 | 100 |
| 65 | — | 40 | 20 | 50 | 50 | 0 | 25 | 50 | 60 | 85 | 0 | — | 20 | 25 |
| 66 | — | 100 | 35 | 70 | 70 | 0 | 75 | 60 | 75 | 100 | 40 | — | 40 | 100 |
| 67 | — | 0 | 0 | 100 | 0 | 0 | 95 | 98 | 100 | 98 | 45 | — | 40 | 95 |

(—) = Not Tested.

The compounds of the present invention are useful as herbicides and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as flowables, as solutions or as any of several other known types of formulations, depending upon the desired mode of application. These formulations may contain as little as about 0.5% to as much as about 95% or more by weight of active ingredient. A herbicidally effective amount depends upon the nature of the seeds or plants to be controlled and the rate of application varies from about 0.01 to approximately 10 pounds per acre, preferably from about 0.02 to about 4 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which may be coated with the toxicant. Granular formulations normally are prepared to contain about 5% to about 25% of active ingredients which may include surface-active agents such heavy aromatic naphthas, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their salts; polyhydric alcohols; polyethoxylated alcohols; esters and fatty amines; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention can be applied to the plants in the conventional manner. Thus, the dust and liquid compositions can be applied to the plant by the use of power-dusters, boom and hand sprayers and spray dusters. The compositions can also be applied from airplanes as a dust or a spray or by rope wick applications because they are effective in very low dosages. In order to modify or control growth of germinating seeds or emerging seedlings, as a typical example, the dust and liquid compositions can be applied to the soil according to conventional methods and can be distributed in the soil to a depth of at least ½ inch below the soil surface. It is not necessary that the phytotoxic compositions be mechanically admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

| EMULSIFIABLE CONCENTRATE FORMULATIONS | | | |
|---|---|---|---|
| General Formula with Ranges | | Specific Formula | |
| Herbicidal compound | 5–55 | herbicidal compound | 24 |
| surfactant(s) | 5–25 | proprietary blend of oil- | 10 |
| solvent(s) | 20–90 | soluble sulfonates and | |
| | 100% | polyoxyethylene ethers | |
| | | polar solvent | 27 |
| | | petroleum hydrocarbon | 39 |
| | | | 100% |

| WETTABLE POWDER FORMULATIONS | | | |
|---|---|---|---|
| herbicidal compound | 3–90 | herbicidal compound | 80 |
| wetting agent | 0.5–2 | sodium dialkyl | 0.5 |
| dispersing agent | 1–8 | naphthalene sulfonate | |
| diluent(s) | 8.5–87 | sodium lignosulfonate | 7 |
| | 100% | attapulgite clay | 12.5 |
| | | | 100% |

| EXTRUDED GRANULAR FORMULATIONS | | | |
|---|---|---|---|
| herbicidal compound | 1–20 | herbicidal compound | 10 |
| binding agent | 0–10 | lignin sulfonate | 5 |
| diluent(s) | 70–99 | calcium carbonate | 85 |
| | 100% | | 100% |

| FLOWABLE FORMULATIONS | | | |
|---|---|---|---|
| herbicidal compound | 20–70 | herbicidal compound | 45 |
| | | polyoxyethylene ether | 5 |
| surfactant(s) | 1–10 | attagel | 0.05 |
| suspending agent(s) | 0.05–1 | propylene glycol | 10 |
| antifreeze agent | 1–10 | 1,2-benzisothiazoline-3-one | 0.03 |
| antimicrobial agent | 1–10 | silicone defoamer | 0.02 |
| antifoam agent | 0.1–1 | water | 39.9 |
| solvent | 7.95–77.85 | | 100% |
| | 100% | | |

The phytotoxic compositions of this invention can also contain other additives, for example, fertilizers, other herbicides and other pesticides, used as adjuvant or in combination with any of the above-described adjuvants. Fertilizers useful in combination with the active ingredients include, for example, ammonium nitrate, urea and superphosphate.

What is claimed is:

1. A compound of the formula wherein
R is halogen, $C_1$–$C_2$ alkyl, $C_1$–$C_2$ alkoxy, nitro; $C_1$–$C_2$ haloalkyl, or $R^aSO_n$— wherein n is 0 or 2 and $R^a$ is $C_1$–$C_2$ alkyl;
$R^1$ is hydrogen or $C_1$–$C_4$ alkyl;
$R^2$ is hydrogen or $C_1$–$C_4$ alkyl;
$R^3$ is hydrogen or $C_1$–$C_4$ alkyl;
$R^4$ is hydrogen or $C_1$–$C_4$ alkyl;
$R^5$ is hydrogen or $C_1$–$C_4$ alkyl;
$R^6$ is hydrogen or $C_1$–$C_4$ alkyl;
$R^7$ and $R^8$ independently are (1) hydrogen; (2) halogen; (3) $C_1$–$C_4$ alkyl; (4) $C_1$–$C_4$ alkoxy; (5) trifluoromethoxy; (6) nitro; (7) $C_1$–$C_4$ haloalkyl; (8) $R^bSO_n$— wherein n is the integer 0, 1 or 2; and $R^b$ is (a) $C_1$–$C_4$ alkyl; (b) $C_1$–$C_4$ alkyl substituted with halogen; (c) phenyl; or (d) benzyl; or (9) —$NR^cR^d$ wherein $R^c$ and $R^d$ independently are hydrogen or $C_1$–$C_4$ alkyl;
$R^9$ is hydrogen or $C_1$–$C_4$ alkyl, $R^{10}$ is (a) hydrogen; (b) $C_1$–$C_6$ alkyl, (c) $C_4$–$C_6$ cycloalkyl, (d) halogen substituted $C_1$–$C_6$ alkyl, (e) phenyl; (f) $C_1$–$C_6$ alkoxy; (g) benzyl; (h) phenethyl; (i) $C_2$–$C_6$ alkenyl; or (j) $C_2$–$C_6$ alkynyl.

2. The compounds of claim 1 wherein R is chlorine, bromine, $C_1C_2$ alkyl, $C_1$-$C_2$ alkoxy, nitro, $C_1$-$C_2$ alkylthio or $C_1$-$C_2$ alkylsulfonyl; $R^1$ is hydrogen or methyl; $R^2$ is hydrogen or methyl; $R^3$ is hydrogen or methy; $R^4$ is hydrogen or methy; $R^5$ is hydrogen or methyl; $R^6$ is hydrogen or methyl; $R^7$ and $R^8$ independently are (1) hydrogen; (2) halogen; (3) $C_1$-$C_4$ alkyl; (4) $C_1$-$C_4$ alkoxy; (5) trifloromethoxy; (6) nitro; (7) $C_1$-$C_4$ haloalkyl; (8) $R^bSO_n$— wherein n is the integer 0, 1 or 2; and $R^b$ is (a) $C_1$-$C_4$ alkyl; (b) $C_1$-$C_4$ alkyl substituted with halogen; (c) phenyl; or (d) benzyl; or (9) —$NR^cR^d$ wherein $R^c$ and $R^d$ independently are hydrogen or $C_1$-$C_4$ alkyl; and $R^9$ is hydrogen or methyl and $R^{10}$ is (a) hydrogen; (b) $C_1$-$C_2$ alkyl; (c) cyclohexyl; (d) $C_1$-$C_4$ alkoxy; (e) phenyl; (f) benzyl; (g) phenethyl; or (h) allyl.

3. The compounds of claim 2 wherein $R^7$ and $R^8$ are independently are hydrogen; chlorine; fluorine; bromine; methyl; methoxy; trifluoromethoxy; nitro; trifluoromethyl; $R^bSO_n$— wherein n is the integer 2 and $R^b$ is methyl, chloromethyl, trifluoromethyl, ethyl, or n-propyl; —$NR^cR^d$ wherein $R^c$ and $R^d$ independently are hydrogen or $C_1$-$C_4$ alkyl; and $R^7$ is in the 3-position.

4. The compound of claim 2 wherein $R^7$ is hydrogen and $R^8$ is hydrogen, chlorine, bromine, fluorine, trifluoromethyl or $R^bSO_2$ wherein $R^b$ is $C_1$-$C_4$ alkyl.

5. The compound of claim 2 wherein R is chlorine; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-chlorine; $R^9$ is methyl; and $R^{10}$ is methoxy.

6. The compound of claim 2 wherein R is nitro; $R^1$ is hydrogen; $R^2$ is hydrogen; $R^3$ is methyl; $R^4$ is methyl; $R^5$ is hydrogen; $R^6$ is hydrogen; $R^7$ is hydrogen; $R^8$ is 4-chlorine; $R^9$ is methyl; and $R^{10}$ is methoxy.

7. The compound of claim 2 wherein R is methyl; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4—$C_2H_5SO_2$—; $R^9$ is ethyl; and $R^{10}$ is ethyl.

8. The compound of claim 2 wherein R is nitro; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-trifluoromethyl; $R^9$ is ethyl; and $R^{10}$ is ethyl.

9. The method of controlling undesirable vegetation comprising applying to the are where control is desired, an herbicidally effective amount of a compound having the formula

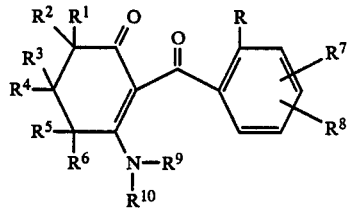

wherein

R is halogen, $C_1$-$C_2$ alkyl, $C_1$-$C_2$ alkoxy, nitro; $C_1$-$C_2$ haloalkyl, or $R^aSO_n$— wherein n is 0 or 2 and $R^a$ is $C_1$-$C_2$ alkyl;

$R^1$ is hydrogen or $C_1$-$C_4$ alkyl;
$R^2$ is hydrogen or $C_1$-$C_4$ alkyl;
$R^3$ is hydrogen or $C_1$-$C_4$ alkyl;
$R^4$ is hydrogen or $C_1$-$C_4$ alkyl;
$R^5$ is hydrogen or $C_1$-$C_4$ alkyl;
$R^6$ is hydrogen or $C_1$-$C_4$ alkyl;
$R^7$ and $R^8$ independently are (1) hydrogen; (2) halogen; (3) $C_1$-$C_4$ alkyl; (4) $C_1$-$C_4$ alkoxy; (5) trifluoromethoxy; (6) nitro; (7) $C_1$-$C_4$ haloalkyl; (8) $R^bSO_n$— wherein n is the integer 0, 1 or 2; and $R^b$ is (a) $C_1$-$C_4$ alkyl; (b) $C_1$-$C_4$ alkyl substituted with halogen; (c) phenyl; or (d) benzyl; or (9) —$NR^cR^d$ wherein $R^c$ and $R^d$ independently are hydrogen or $C_1$-$C_4$ alkyl;

$R^9$ is hydrogen or $C_1$-$C_4$ alkyl, $R^{10}$ is (a) hydrogen; (b) $C_1$-$C_6$ alkyl, (c) $C_4$-$C_6$ cycloalkyl, (d) halogen substituted $C_1$-$C_6$ alkyl, (e) phenyl; (f) $C_1$-$C_6$ alkoxy; (g) benzyl; (h) phenethyl; (i) $C_2$-$C_6$ alkenyl; or (j) $C_2$-$C_6$ alkynyl.

10. The method of claim 9 wherein R is chlorine, bromine, $C_1C_2$ alkyl, $C_1$-$C_2$ alkoxy, nitro, $C_1$-$C_2$ alkylthio or $C_1$-$C_2$ alkylsulfonyl; $R^1$ is hydrogen or methyl; $R^2$ is hydrogen or methyl; $R^3$ is hydrogen or methyl; $R^4$ is hydrogen or methyl; $R^5$ is hydrogen or methyl; $R^6$ is hydrogen or methyl; $R^7$ and $R^8$ independently are (1) hydrogen; (2) halogen; (3) $C_1$-$C_4$ alkyl; (4) $C_1$-$C_4$ alkoxy; (5) trifloromethoxy; (6) nitro; (7) $C_1$-$C_4$ haloalkyl; (8) $R^bSO_n$— wherein n is the integer 0, 1 or 2; and $R^b$ is (a) $C_1$-$C_4$ alkyl; (b) $C_1$-$C_4$ alkyl substituted with halogen; (c) phenyl; or (d) benzyl; or (9) —$NR^cR^d$ wherein $R^c$ and $R^d$ independently are hydrogen or $C_1$-$C_4$ alkyl; and $R^9$ is hydrogen or methyl and $R^{10}$ is (a) hydrogen; (b) $C_1$-$C_2$ alkyl; (c) cyclohexyl; (d) $C_1$-$C_4$ alkoxy; (e) phenyl; (f) benzyl; (g) phenethyl; or (h) allyl.

11. The method of claim 10 wherein $R^7$ and $R^8$ are independently are hydrogen; chlorine; fluorine; bromine; methyl; methoxy; trifluoromethoxy; nitro; trifluoromethyl; $R^bSO_n$— wherein n is the integer 2 and $R^b$ is methyl, chloromethyl, trifluoromethyl, ethyl, or n-propyl; —$NR^cR^d$ wherein $R^c$ and $R^d$ independently are hydrogen or $C_1$-$C_4$ alkyl; and $R^7$ is in the 3-position.

12. The method of claim 10 wherein $R^7$ is hydrogen and $R^8$ is hydrogen; chlorine; bromine; fluorine; trifluoromethyl; or $R^bSO_2$ wherein $R^b$ is $C_1$-$C_4$ alkyl.

13. the method of claim 10 wherein R is chlorine; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-chlorine; $R^9$ is methyl; and $R^{10}$ is methoxy.

14. The method of claim 10 wherein R is nitro; $R^1$ is hydrogen; $R^2$ is hydrogen; $R^3$ is methyl; $R^4$ is methyl; $R^5$ is hydrogen; $R^6$ is hydrogen; $R^7$ is hydrogen; $R^8$ is 4-chlorine; $R^9$ is methyl; and $R^{10}$ is methoxy.

15. The method of claim 12 wherein R is methyl; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4—$C_2H_5SO_2$—; $R^9$ is ethyl; and $R^{10}$ is ethyl.

16. The method of claim 10 wherein R is nitro; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-trifluoromethyl; $R^9$ is ethyl; and $R^{10}$ is ethyl.

17. A herbicidal composition comprising a substituted 3-amino-2-benzoyl-cyclohex-2-enone compound of the formula

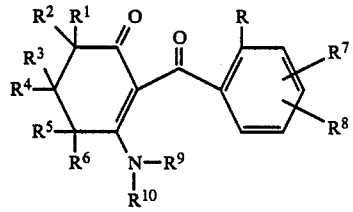

wherein

R is halogen, $C_1$–$C_2$ alkyl, $C_1$–$C_2$ alkoxy, nitro; $C_1$–$C_2$ haloalkyl, or $R^aSO_n$— wherein n is 0 or 2 and $R^a$ is $C_1$–$C_2$ alkyl;

$R^1$ is hydrogen or $C_1$–$C_4$ alkyl;
$R^2$ is hydrogen or $C_1$–$C_4$ alkyl;
$R^3$ is hydrogen or $C_1$–$C_4$ alkyl;
$R^4$ is hydrogen or $C_1$–$C_4$ alkyl;
$R^5$ is hydrogen or $C_1$–$C_4$ alkyl;
$R^6$ is hydrogen or $C_1$–$C_4$ alkyl;
$R^7$ and $R^8$ independently are (1) hydrogen; (2) halogen; (3) $C_1$–$C_4$ alkyl; (4) $C_1$–$C_4$ alkoxy; (5) trifluoromethoxy; (6) nitro; (7) $C_1$–$C_4$ haloalkyl; (8) $R^bSO_n$— wherein n is the integer 0, 1 and 2; and $R^b$ is (a) $C_1$–$C_4$ alkyl; (b) $C_1$–$C_4$ alkyl substituted with halogen; (c) phenyl; or (d) benzyl; or (9) —$NR^cR^d$ wherein $R^c$ and $R^d$ independently are hydrogen or $C_1$–$C_4$ alkyl;
$R^9$ is hydrogen or $C_1$–$C_4$ alkyl, $R^{10}$ is (a) hydrogen; (b) $C_1$–$C_6$ alkyl, (c) $C_4$–$C_6$ cycloalkyl, (d) halogen substituted $C_1$–$C_6$ alkyl, (e) phenyl; (f) $C_1$–$C_6$ alkoxy; (g) benzyl; (h) phenethyl; (i) $C_2$–$C_6$ alkenyl; or (j) $C_2$–$C_6$ alkynyl and an inert carrier therefor.

18. The composition of claim 17 wherein R is chlorine, bromine, $C_1C_2$ alkyl, $C_1$–$C_2$ alkoxy, nitro, $C_1$–$C_2$ *alkylthio or* $C_1$–$C_2$ alkylsulfonyl; $R^1$ is hydrogen or methyl; $R^2$ is hydrogen or methyl; $R^3$ is hydrogen or methyl; $R^4$ is hydrogen or methyl; $R^5$ is hydrogen or methyl; $R^6$ is hydrogen or methyl; $R^7$ and $R^8$ independently are (1) hydrogen; (2) halogen; (3) $C_1$–$C_4$ alkyl; (4) $C_1$–$C_4$ alkoxy; (5) trifloromethoxy; (6) nitro; (7) $C_1$–$C_4$ haloalkyl; (8) $R^bSO_n$— wherein n is the integer 0, 1 or 2; and $R^b$ is (a) $C_1$–$C_4$ alkyl; (b) $C_1$–$C_4$ alkyl substituted with halogen; (c) phenyl; or (d) benzyl; or (9) —$NR^cR^d$ wherein $R^c$ and $R^d$ independently are hydrogen or $C_1$–$C_4$ alkyl; and $R^9$ is hydrogen or methyl and $R^{10}$ is (a) hydrogen; (b) $C_1$–$C_2$ alkyl; (c) cyclohexyl; (d) $C_1$–$C_4$ alkoxy; (e) phenyl; (f) benzyl; (g) phenethyl; or (h) allyl.

19. The composition of of claim 17 wherein $R^7$ and $R^8$ are independently are hydrogen; chlorine; fluorine; bromine; methyl; methoxy; trifluoromethoxy; nitro; trifluoromethyl; $R^bSO_n$— wherein n is the integer 2 and $R^b$ is methyl, chloromethyl, trifluoromethyl, ethyl, or n-propyl; —$NR^cR^d$ wherein $R^c$ and $R^d$ independently are hydrogen or $C_1$–$C_4$ alkyl; and $R^7$ is in the 3-position.

20. The composition of claim 1 wherein $R^7$ is hydrogen and $R^8$ is hydrogen; chlorine; bromine; fluorine; trifluoromethyl; or $R^bSO_2$ wherein $R^b$ is $C_1$–$C_4$ alkyl.

21. The composition of claim 1 wherein R is chlorine; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-chlorine; $R^9$ is methyl; and $R^{10}$ is methoxy.

22. The composition of claim 17 wherein R is nitro; $R^1$ is hydrogen; $R^2$ is hydrogen; $R^3$ is methyl; $R^4$ is methyl; $R^5$ is hydrogen; $R^6$ is hydrogen; $R^7$ is hydrogen; $R^8$ is 4-chlorine; $R^9$ is methyl; and $R^{10}$ is methoxy.

23. The composition of claim 17 wherein R is methyl; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4—$C_2H_5SO_2$—; $R^9$ is ethyl; and $R^{10}$ is ethyl.

24. The composition of claim 17 wherein R is nitro; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-trifluoromethyl; $R^9$ is ethyl; and $R^{10}$ is ethyl.

* * * * *

UNITED STATES PATENT AND TRADEMARK OFFICE
CERTIFICATE OF CORRECTION

PATENT NO. : 4,775,411

DATED : October 4, 1988

INVENTOR(S) : Christopher G. Knudsen

It is certified that error appears in the above-identified patent and that said Letters Patent is hereby corrected as shown below:

In Column 10, for Compound No. 51, the entry under column $R^{10}$ which reads "$HCC-CH_2-$" should read --- $-HC \equiv C-CH_2-$ ---.

In Column 10, for Compound No's. 52 and 53, the entries under column $R^{10}$ which read "$NC-CH_2CH_2-$" should read --- $N \equiv C-CH_2CH_2-$ ---.

In Column 19, at line 43, the word "are" should read ---area---.

Signed and Sealed this

Tenth Day of December, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,775,411

DATED : October 4, 1988

INVENTOR(S) : Christopher G. Knudsen

It is certified that error appears in the above-identified patent and that said Letters Patent is hereby corrected as shown below:

On the title page, first column, under Attorney, Agent, or Firm, the name "Edwin H. Basker" should read ---Edwin H. Baker---.

In the Abstract, at line 16 after the formula, the word "alkogxy" should read ---alkoxy---.

In Column 10, for Compound No's. 20, 21, 22, 27, 32, 33, 34 and 35 the entries under the column $R^{10}$ should bridge between columns $R^9$ and $R^{10}$.

In Column 11, for Compound No's. 68, 69, 70 and 71, the entries under the column $R^4$ should bridge between columns $R^3$ and $R^4$.

In Column 12, for Compound No. 68 the entry under the column $R^{10}$ should bridge between columns $R^9$ and $R^{10}$.

In Column 20: at line 38, the word "the" should read ---The---; and
at line 46, the number "12" should read ---10---.

In Column 21: at line 24, the phrase "$C_1C_2$" should read ---$C_1$-$C_2$---, and the phrase "$C_1$-$C_2$1" should read ---$C_1$-$C_2$---; and
at line 30, the word "trifloromethoxy" should read ---trifluoromethoxy---.

UNITED STATES PATENT AND TRADEMARK OFFICE
CERTIFICATE OF CORRECTION

PATENT NO. : 4,775,411

DATED : October 4, 1988

INVENTOR(S) : Christopher G. Knudsen

It is certified that error appears in the above-identified patent and that said Letters Patent is hereby corrected as shown below:

In Column 22, at lines 13 & 16, the number "1" should read ---17---.

Signed and Sealed this

Eleventh Day of February, 1992

Attest:

Attesting Officer

HARRY F. MANBECK, JR.

Commissioner of Patents and Trademarks